United States Patent [19]

Burns et al.

[11] Patent Number: 4,845,036

[45] Date of Patent: Jul. 4, 1989

[54] PROCESS FOR ISOLATION OF THE B OLIGOMER OF PERTUSSIS TOXIN

[75] Inventors: Drusilla L. Burns, Washington, D.C.; Charles R. Manclark, Rockville, Md.

[73] Assignee: The United States of America as represented by the Department of Health and Human Services, Washington, D.C.

[21] Appl. No.: 10,467

[22] Filed: Feb. 3, 1987

[51] Int. Cl.$^4$ ............................................. C12N 9/12
[52] U.S. Cl. ...................... 435/194; 424/92; 435/183; 435/193; 530/403; 530/415; 530/416; 530/825
[58] Field of Search .............. 435/183, 193, 194; 424/92; 530/403, 415, 416, 825

[56] References Cited

U.S. PATENT DOCUMENTS

| | | |
|---|---|---|
| 2,772,201 | 11/1946 | Tint . |
| 4,029,766 | 6/1977 | Helting .............................. 424/92 |
| 4,435,386 | 3/1984 | Ribi et al. ........................ 424/177 |
| 4,436,727 | 3/1984 | Ribi .................................. 424/177 |
| 4,436,728 | 3/1984 | Ribi et al. ........................ 424/177 |
| 4,705,686 | 11/1987 | Scott et al. ....................... 424/92 |
| 4,774,086 | 9/1988 | Quentin-Millet et al. ........ 424/92 |

OTHER PUBLICATIONS

Wong et al., "Pertussis Toxin Substrate is a Guanosine 5'-[$\beta$-thio] Diphosphate-N-Ethylmaleimide–, $Mg^{+2}$-and Temperature-Sensitive GTP-Binding Protein," Biochem. J., 1985, 232(1), 191-7.

Burns et al., "Adenine Nucleotides Promote Dissociation of Pertussis Toxin Subunits", J. Biol. Chem., 1986, 261(9), 4324-7.

Biochemistry (1982), vol. 21, pp. 5516-5522.

Primary Examiner—Robert A. Wax
Attorney, Agent, or Firm—Browdy and Neimark

[57] ABSTRACT

A method for dissociating the B oligomer of pertussis toxin comprising incubating pertussis toxin in an aqueous solution of urea, sodium phosphate buffer, and a nucleotide selected from the group consisting of ATP and ADP, and optional zwitterionic detergent; applying the incubated solution to a CM-Sepharose column; and eluting the B oligomer from the column with potassium phosphate buffer containing urea.

6 Claims, No Drawings

PROCESS FOR ISOLATION OF THE B OLIGOMER OF PERTUSSIS TOXIN

FIELD OF THE INVENTION

The present invention relates to a method for isolating the B oligomer of pertussis toxin.

BACKGROUND OF THE INVENTION

An "A-B" model has been proposed for several toxic peptides that cross cell membranes; any of these peptides, including cholera, pertussis, and diphtheria toxins, consists of two functionally distinct parts, an A component that is active enzymatically and a B component that binds to surface receptors to enable the A component to enter the cell where it acts. The interaction of these toxins with intact cells is characterized by a lag time that precedes the onset of their action, probably a time required for the A component to traverse the plasma membranes. In the case of IAP, there was a definite lag period of one hour before alpha-adrenergic inhibition of insulin secretion began to be reversed progressively in islet cultures with isletactivating protein, IAP.

Pertussis toxin, an exotoxin produced by *Bordetella pertussis*, comprises these two components: an enzymatically active A subunit and a B oligomer which is responsible for binding of the toxin to eukaryotic cell surfaces. The B oligomer, composed of five subunits ranging in molecular weights from 23,000 to 9,300, exhibits certain activities. For example, the B oligomer agglutinates erythrocytes and stimulates mitosis of lymphocytes. The A subunit, a single polypeptide chain having a molecular weight of 28,000, catalyzes the ADP-ribosylation of a family of GTP-binding regulatory proteins found in eukaryotic cells. In the absence of a protein substrate, the A subunit will catalyze the hydrolysis of NAD to ADP-ribose and nicotinamide. The ADP-ribosyltransferase activity of the toxin is believed to be responsible for a number of biological effects observed both in vivo and in vitro. For example, ADP-ribosylation of the GTP-binding protein termed $G_i$ can result in interference with the ability of the cell to respond to hormones which inhibit cyclic AMP production or mobilize calcium.

Pertussis toxin resembles cholera toxin and diphtheria toxin in that it comprises two types of components, one enzymatically active and the other responsible for the binding of the toxin to the eukaryotic cell surface and the introduction of the active subunit into the cell. The holotoxin and the isolated A subunit have been described to be equally effective on a molar basis in ADP-ribosylating $G_i$ in crude membrane preparations from certain cell types such as C6 glioma cells. However, only the subunit and not the holotoxin was reported to be effective in transferring the ADP-ribose moiety of NAD to $G_i$ in crude membrane preparations of rabbit platelets and rat mast cells. Moreover, the A subunit is more active than the holotoxin on a molar basis in catalyzing the hydrolytic cleavage of NAD to ADP-ribose and nicotinamide in vitro.

Tamura et al. in *Biochemistry* 21;5516–5522, 1982, describe the analysis of the B oligomer of pertussis toxin by degrading the toxin with sodium dodecyl sulfate followed by gel electrophoresis. The subunits were separated by exposure of the material to 5M ice-cold urea for four days, followed by column chromatography with carboxymethyl-Sepharose. This yielded sharp separation of S-1 and S-5, leaving the other subunits as two dimers. These dimers were then dissociated into their constituent subunits, S-2 and S-4 for one dimer and S-3 and S-4 for the other, after sixteen hours of exposure to 8 M urea. These subunits were obtained individually upon further chromatography on a diethylaminoethyl-Sepharose column. Subunits other than S-1 were adsorbed as a pentamer by a column using haptoglobin as an affinity adsorbent. The same pentamer was obtained by adding S-5 to the mixture of two dimers. Neither this pentamer nor other oligomers exhibited biological activity in vivo. Recombination of S-1 with the pentamer at the 1:1 molar ratio yielded a hexamer which was identical with the native toxin in electrophoretic mobility and biological activity to enhance glucose-induced insulin secretion when injected into rats.

In Japanese patent No. 59110626 is described a pertussis vaccine containing, as the active ingredient, the B oligomer of pertussis toxin. Aluminum phosphate or aluminum hydroxide is incorporated as an adjuvant. The new vaccine disclosed is free from side effects and does not substantially contain any endotoxin, and has a higher phylaxis effect.

Helting, in U.S. Pat. No. 4,029,766, discloses a method for making a protective antigen from *Bordetella pertussis* by mixing the pathogens with an aqueous solution of a denaturing agent and a neutral salt, separating the liquid supernatant containing the protective antigen suspended therein from the residue, and subsequently separating the denaturing agent from the aqueous suspension of the protective antigen.

Tint, in U.S. Pat. No. 2,772,201, discloses a method for fractionating and concentrating proteins of bacterial origin, such as from pertussis, by precipitation of all of the protein complex molecules having an isoelectric pH equal to or higher than that of the active protein, separating them from the solution, and fractionating them.

Ribi et al., in U.S. Pat. No. 4,435,386, and Ribi in U.S. Pat. Nos. 4,436,727 and 4,436,728, disclose a method of making a refined detoxified endotoxin product by reacting endotoxic extract with an inorganic or organic acid and lyophilizing to produce a hydrolyzed crude lipid A. This product is treated with a solvent to dissolve out impurities.

In Japanese Patent No. 53222032, there is described the use of pertussis subunits S2, S3, and S4 in a vaccine.

SUMMARY OF THE INVENTION

It is an object of the present invention to overcome the aforementioned deficiencies in the prior art.

It is another object of the present invention to provide a simple and effective method for isolating the B oligomer of pertussis toxin, which B oligomer can be used to produce a pertussis vaccine.

The B oligomer of pertussis toxin can be obtained in a form dissociated from the A subunit by incubation of pertussis toxin in sodium phosphate buffer, pH 7, containing urea with optional zwitterionic detergent. The solution is then applied to CM Sepharose CL-6B Carboxymethyl Sepharose is obtained by introducing crboxymethyl groups to Sepharose CL. Sephorose CL is obtained by crosslinking agarose with 2,3-dibromopropanol (cf. U.K. Pat. No. 1,352,613) and desulfating the resulting gel by alkaline hydrolysis under reducing condition (J. Chromatogr. 60 (1971) 167–177). The B oligomer is eluted from the column with potassium phosphate buffer, pH 7.5, containing urea.

The process of the present invention thus allows for the isolation of four pertussis subunits, S2, S3, S4, and S5, which subunits associate to form a complex.

DETAILED DESCRIPTION OF THE INVENTION

EXAMPLE I

Pertussis toxin was purified from culture supernatants of *B. pertussis* 114 as described by Sekura et al., J. Biol. Chem. 258:14647-14651, 1983. The A subunit was dissociated from the B oligomer by incubation in 10mM sodium phosphate buffer, pH 7, containing 3M urea, 1% CHAPS (3-[Cholamidopropy)-dimethylammonio-]-1propanesulfonate, and 100 micromolar ATP (buffer A) for 15 minutes. The solution containing 1.0 mg of protein was applied to a column (0.38 $cm^2$ by 2 cm) of carboxymethyl Sepharose CL-6B (Pharmacia, Uppsala, Sweden) which had been equilibrated with buffer A. The A subunit did not bind to the column and was eluted with an additional 0.8 ml of buffer A. The column was then washed with 6 volumes of buffer A. The B oligomer was eluted from the column with 1.0 ml of 0.2M potassium phosphate buffer, pH 7.5, containing 2M urea.

The extent of contamination of the A subunit preparation with B oligomer was measured by testing for hemagglutination activity. The A subunit preparation exhibited hemagglutination activity at a concentration of 10 micrograms/ml. whereas the B oligomer preparation agglutinated erythrocytes at a concentration of 0.044 micrograms/ml, suggesting that the A preparation contained 0.44% B oligomer by weight.

The extent of contamination of the B oligomer preparation with the A subunit was determined by measuring ADP-ribosyltransferase activity. A three microgram amount of the B oligomer exhibited ADP-ribosyltransferase activity equivalent to that exhibited by 50 ng of the holotoxin (of which 12 ng is A subunit). Thus, the B oligomer preparation contains approximately 0.4% A subunit by weight.

The pertussis toxin could be modified with N-ethylmaleimide, which prevented the A subunit from reassociating with the B oligomer. Pertussis toxin at a concentration of 0.33 mg/ml was incubated in 50 mM potassium phosphate, pH 7.5, containing 2mM dithiothreitol, 3M urea, 0.1 mM ATP, and 1% CHAPS for three hours at room temperature to dissociate the A subunit from the B oligomer. A solution of N-ethylmaleimide (Sigma Chemical Co., St. Louis, Mo.) in water was then added so that the final concentration of N-ethylmaleimide was 6 mM ( a total of 1.5 micromoles), and the protein concentration was 0.25 mg/ml. After incubation at room temperature for one hour, the reaction was stopped by the addition of 1.5 micromole of dithiothreitol. Preliminary experiments indicated that, after modification with Nethylmaleimide, the A subunit did not readily reassociate with the B oligomer.

EXAMPLE II

Pertussis toxin was purified from the culture supernatant of *Bordetella pertussis* 114 as described by Sekura et al. in J. Biol. Chem. 258, 14647-14651, 1983. The A subunit was separated from the B oligomer by treatment with sodium phosphate buffer as follows.

The pertussis toxin, 0.34 mg in 0.5 ml of 5 mM sodium phosphate buffer containing 2.1 M urea and 100 micromolar ATP, was added to a microcentrifuge tube containing 0.3 ml of packed CM-Sepharose which had been equilibrated with the same buffer. After 15 minutes of incubation at room temperature, the tube was centrifuged at 12,800× g for 1 minute. The supernatant containing the A subunit was removed. The CM-Sepharose (carboxymethyl Sepharose, was washed four times with one ml of buffer. Each wash was discarded. The B oligomer was removed by addition of 0.6 ml of 0.2 M potassium phosphate buffer, pH 7.5, containing 2 M urea. Fractions containing the A and B subunits were dialyzed extensively against 50 mM sodium phosphate, pH 7, containing 2 M urea.

In order to determine the extent of subunit dissociation promoted by the ATP and its analogs, forty microliters of packed CM-Sepharose were washed once with 0.5 ml of 5 mM sodium phosphate, pH 7, containing 0.1 mg/ml ovalbumin in a microcentrifuge tube. After centrifugation at 12,800 × g for one minute, the supernatant was discarded. The CM-Sepharose (carboxymethyl Sepharose) was then washed three times with 0.5 ml of 7 mM sodium phosphate, pH 7, containing 1% CHAPS. Pertussis toxin in 10.5 microliters of 0.1 M sodium phosphate, pH 7, containing 2 M urea, was diluted with water containing adenine nucleotides to give a final volume of 150 microliters. After fifteen minutes at room temperature, the toxin mixture was added to the CM-Sepharose (carboxymethyl Sepharose) and incubated at room temperature for fifteen minutes. The preparation was then centrifuged at 12,800× g for one minute, and the supernatant, 130 microliters, containing free A subunit, was removed and saved. The CM-Sepharose (carboxymethyl Sepharose) was then washed once with 7 mM sodium phosphate, pH 7, containing CHAPS, and adenine nucleotides. After centrifugation, this wash was discarded. The protein which remained bound to the CM-Sepharose (carboxylmethyl Sepharose) (holotoxin and B oligomer) was released by addition of 150 microliters of 0.1 M Tris base containing 2 M urea. After centrifugation, 130 microliters of the supernatant was removed and saved. The fraction containing the A subunit and that containing B oligomer and holotoxin were subjected to electrophoresis on polyacrylamide gels containing SDS as described by Laemmli in *Nature New. Biol.* 227, 680-685, 1970.

When pertussis toxin was incubated with either ATP or CHAPS and then added to CM-Sepharose, the vast majority of both A and B subunits bound to the CM-Sepharose, indicating that the toxin remained intact under these conditions. However, in the presence of both ATP and CHAPS, a significant amount of the A subunit does not bind to the CM-Sepharose and therefore has dissociated form the B oligomer. ATP has been found to induce dissociation of pertussis toxin subunits in the absence of CHAPS if at relatively high concentration (>1 M) of urea are present.

The amount of ATP needed to promote dissociation of subunits was found to be in the micromolar range, generally from about 1 to about 10 micromolar. It was found that 0.1 micromolar ATP had little effect on the dissociation of subunits, whereas concentration of 1 micromole and greater promoted release of the A subunit from the B oligomer. Similar concentrations of ATP promoted stimulation of NAD glycohydrolase activity. Both ATP and ADP will promote subunit dissociation of pertussis toxin. These nucleotides also activate NAD glycohydrolase activity of the protein. AMP and adenosine were without effect on both subunit dissociation and NAD glycohydrolase activity.

Other nucleotide triphosphates were found not to be as potent as ATP in inducing subunit dissociation or in stimulating NAD glycohydrolase activity.

It has thus been found that, in the presence of the zwitterionic detergent, CHAPS, ATP weakens the intersubunit bonds between the A subunit and B oligomer. A strong correlation exists between subunit dissociation and NAD glycohydrolase activity. Similarly, those adenine nucleotides which stimulate enzymatic activity, such as ATP and ADP, are effective in inducing subunit dissociation. AMP and adenosine did not detectably alter in subunit bond strength or NAD glycohydrolase activity.

The B oligomer prepared according to the present invention possesses the biological activities normally associated with the binding components of the toxin. The B oligomer was as effective on a molar basis as the holotoxin in agglutinating goose erythrocytes. The minimum concentrations required for hemagglutination of pertussis toxin and B oligomer were 0.67 and 0.49 pmol/ml, respectively. In addition, the isolated B oligomer exhibited the ability to stimulate lymphocyte mitosis, although it was only 40% as effective as the holotoxin on a molar basis. The concentrations required for maximal mitogenic activity of pertussis toxin and B oligomer were 21 and 56 pmol/ml, respectively. In the absence of mitogen, [$^3$H]thymidine was incorporated to the extent of 250 cpm/$2 \times 10^5$ cells. Incorporation in the presence of pertussis toxin and B oligomer was 9,000 and 10,700 cpm/$2 \times 10^5$ cells, respectively.

Various modifications of the toxin will result in perturbation of its enzymatic activity reflecting alterations in the A subunit, and of its hemagglutination activity, indicating changes in the B oligomer. The NAD glycohydrolase activity of toxin was significantly decreased when the protein was modified with glutaraldehyde or N-ethylmaleimide. The hemagglutination activity of toxin modified by exposure to glutaraldehyde or UV light was decreased. Thus, the modified toxins were altered in the A subunit, B oligomer, or both.

The B oligomer of pertussis toxin is useful as a component of acellular pertussis vaccines, having none of the side effects of the prior vaccines containing the endotoxin.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning an range of equivalents of the disclosed embodiments. It is to be understood that the phraseology or terminology employed herein is for the purpose of description and not of limitation.

What is claimed is:

1. A method for dissociating the B oligomer of pertussis toxin from the A subunit of pertussis toxin comprising:

incubating pertussis toxin in an aqueous solution comprising sodium phosphate buffer.ph 7.0, about 3M urea, and a nucleotide selected from the group consisting of ADP and ATP said nucleotide being from about 1 to about 10 micromolar;

applying the incubated solution to a CM-Shpharose column;

eluting B oligomer from the column with potassium phosphate buffer containing urea.

2. The method of claim 1 wherein the nucleotide is ATP.

3. The method of claim 1 wherein the aqueous solution further includes a zwitterionic detergent.

4. The method of claim 3 wherein the nucleotide is ATP.

5. The method of clime 3 wherein the zwitterionic detergent is 3-[(3-cholamidopropyl)-dimethylammonio]-1-propane sulfonate.

6. A method of modifying pertussis toxin comprising adding to said N-ethylmaleimide in an amount sufficient to prevent the B oligomer from reassociating with A subunit of pertussis toxin.

* * * * *